United States Patent [19]

Doi et al.

[11] Patent Number: 5,567,608
[45] Date of Patent: Oct. 22, 1996

[54] BIOCATALYSTS IMMOBILIZED IN A STORAGE STABLE COPOLYMER GEL

[75] Inventors: Toshiaki Doi; Hiroyasu Bamba; Kouzou Murao, all of Kanagawa, Japan

[73] Assignee: Nitto Chemical Industry Co., Ltd., Tokyo, Japan

[21] Appl. No.: 370,254

[22] Filed: Jan. 9, 1995

[30] Foreign Application Priority Data

Jan. 11, 1994 [JP] Japan .................. 6-012279

[51] Int. Cl.$^6$ ................. C12N 11/04; C12N 11/08
[52] U.S. Cl. ........................... 435/182; 435/180
[58] Field of Search .......................... 435/180, 182; 436/535; 530/817

[56] References Cited

U.S. PATENT DOCUMENTS

| | | | |
|---|---|---|---|
| 4,421,855 | 12/1983 | Watanabe et al. | 435/129 |
| 4,526,867 | 7/1985 | Chibata et al. | 435/178 |
| 4,975,375 | 12/1990 | Haruta et al. | 435/482 |
| 5,200,471 | 4/1993 | Coleman et al. | 525/326.9 |
| 5,226,902 | 7/1993 | Bae et al. | 604/892.1 |

FOREIGN PATENT DOCUMENTS

| | | |
|---|---|---|
| 0494554 | 7/1992 | European Pat. Off. . |
| 2268818 | 11/1975 | France . |
| WO9314133 | 7/1993 | WIPO . |

OTHER PUBLICATIONS

Chibata et al., "Immobilized Aspartase–Containing Microbial Cells; Preparation and Enzymatic Properties", Applied Microbiology, May 1974, pp. 878–885.

Hattori et al, "Chemical Activities of *E. Coli* Adsorbed On a Resin", The Journal of Biochemistry, vol. 48, No. 6, 1960, pp. 831–837.

*Primary Examiner*—David M. Naff
*Attorney, Agent, or Firm*—Sughrue, Mion, Zinn, Macpeak & Seas

[57] ABSTRACT

Biocatalysts such as cells and enzymes are immobilized in a polymer gel by forming a mixture containing a biocatalyst, an N,N-dialkylacrylamide monomer, a cationic acrylamide monomer and a water-soluble cross-linking monomer, and copolymerizing the monomers to produce a polymer gel entrapping the biocatalyst. Preferably, the N, N-dialkylacrylamide is N,N-dimethylacrylamide or N,N-diethylacrylamide in an amount of about 70 to about 99.8% by weight, the cationic acrylamide monomer is N,N-dimethylaminopropylacrylamide, N,N-dimethylaminopropylmethacrylamide, N,N-diethylaminopropylmethacrylamide, N,N-diethylaminopropylacrylamide and quaternary compounds thereof in a amount of about 0.1 to about 10% by weight and the cross-linking monomer is N,N'-methylenebisacrylamide, N,N'-methylenebismethacrylamide, N,N'-(1,2-dihydroxyethylene)bisacrylamide, 1,3-diacrylamide methyl-2-imidazolidone or diacrylamide methylene urea in an amount of about 0.1 to about 20% by weight. The polymer gel containing a biocatalyst has excellent storage stability and does not putrefy even after one month of storage at ordinary temperature.

6 Claims, No Drawings

BIOCATALYSTS IMMOBILIZED IN A STORAGE STABLE COPOLYMER GEL

FIELD OF THE INVENTION

This invention relates to a carrier for use in the immobilization of biocatalysts, to an immobilized biocatalyst obtained by entrapping the biocatalyst in the carrier, and to a method for immobilizing the biocatalyst.

BACKGROUND OF THE INVENTION

When biocatalysts are used on an industrial scale, they are usually used in an immobilized form with the objectives of preventing elution of impurities from the biocatalyst, improving separability of the biocatalyst from the reaction product, improving applicability of the biocatalyst to repeated use, increasing enzymatic stability of the biocatalyst, and carrying out continuous operation of the production steps.

Immobilization of biocatalysts is effected by a carrier binding method, a cross-linking method, an entrapping immobilization method and the like (cf. T. Hattori and C. Frusaka, *J. Biochem.*, vol. 48, pp. 831 (1960)), of which the entrapping immobilization method is most advantageous in that leakage of biocatalysts is small, and a decrease in the biocatalyst activity caused by the immobilization process is also small, because the biocatalyst and its carrier are not linked to each other. Furthermore, the method can be applied to the immobilization of a large variety of biocatalysts.

Examples of known carriers for use in the entrapping immobilization of biocatalysts include synthetic, high polymers such as polyacrylamide, polyvinyl alcohol, polyurethane, collagen, a photosetting resin and the like, and natural, high polymers such as carrageenan, alginic acid, agarose, gelatin, starch and the like (cf. U.S. Pat. No. 4,526,867). In general, in comparison with the natural, high polymers, the synthetic, high polymers are high in strength, excellent in durability and resistant to biodegradation. Of these, polyacrylamide is used most frequently because it is industrially inexpensive, has high polymer strength and causes less inactivation of biocatalysts at the time of polymerization (cf. U.S. Pat. No. 4,421,855 and I. Chibata, T. Tosa and T. Sato, *Appl. Microbiol.*, vol. 27, pp. 878 (1974)).

In addition, a process has been proposed in which acrylamide, a cationic ethylenic unsaturated monomer, and a water-soluble cross-linking monomer are subjected to copolymerization in order to reduce degree of swelling of a polyacrylamide base immobilized biocatalyst obtained by the entrapping immobilization method and to reduce inactivation of the catalyst at the time of the reaction (cf. JP-B-58-35078; the term "JP-B" as used herein means an "examined Japanese patent publication").

However, such polyacrylamide base immobilized biocatalysts, obtained by the entrapping immobilization method, are generally stored by soaking in an aqueous solution such as a buffer solution or the like, since their activities are apt to decrease when exposed to air oxidation or drying. When the storage is continued at room temperature for a prolonged period of time (for example, more than 1 month), the storing solution and the biocatalyst start to putrefy which causes generation of offensive odors from, and turbidity in, the storing solution and causes a decrease in the activity to such a level that it cannot be used as a catalyst. As a consequence, their storage is effected generally by putting them in a refrigerator or adding an antiseptic agent to the storing solution.

However, the cold storage method requires a huge cost for facilities, utilities and the like when biocatalysts are used in an industrially large quantity, and the other method, in which an antiseptic agent is added to the storing solution, causes permeation of the antiseptic agent itself into the immobilized biocatalyst, thereby adversely effecting the quality of products for the practical use.

It is important to overcome these problems especially in the case of the industrial application of immobilized biocatalysts.

SUMMARY OF THE INVENTION

The inventors of the present invention have conducted intensive studies on the development of a biocatalyst-immobilizing method which not only has the advantages of the prior art polyacrylamide base carriers but also is excellent in storage stability, and as a result, have found that the use of a specified copolymer, as a carrier, is markedly effective in overcoming the aforementioned problems. The present invention has been accomplished on the basis of this finding.

Accordingly, the present invention comprises a carrier for use in the immobilization of biocatalysts which is obtained by copolymerizing a first monomer represented by the following general formula (1) with a cationic acrylamide monomer and a water-soluble cross-linking monomer, both being capable of copolymerizing with the first monomer:

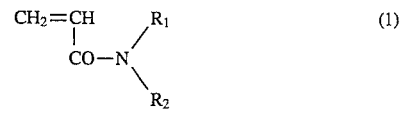

wherein each of $R_1$ and $R_2$ represents a methyl group or an ethyl group, an immobilized biocatalyst which is obtained by entrapping a biocatalyst in the carrier for biocatalyst immobilization use as well as a method for immobilizing a biocatalyst.

Other objects and advantages of the present invention will be made apparent as the description of the invention progresses.

DETAILED DESCRIPTION OF THE INVENTION

Illustrative examples of the compound represented by the aforementioned general formula (1) include N,N-dimethylacrylamide, N,N-diethylacrylamide and N-methyl-N-ethylacrylamide, which may be used alone or as a mixture of two or more compounds.

Illustrative examples of the cationic acrylamide monomer capable of copolymerizing with the monomer of general formula (1) include N,N-dialkylaminoalkyl methacrylamides, N,N-dialkylaminoalkylacrylamides and quaternary compounds thereof, such as N,N-dimethylaminopropylacrylamide, N,N-dimethylaminopropyl methacrylamide, N,N-diethylaminopropyl methacrylamide, N,N-diethylaminopropylacrylamide and quaternary compounds thereof.

Illustrative examples of the water-soluble cross-linking monomer include N,N'-methylenebisacrylamide, N,N'-methylenebismethacrylamide, N,N'-(1,2-dihydroxyethylene)bisacrylamide, 1,3-di-acrylamide methyl-2-imidazolidone, diacrylamide methylethylene urea, diacrylamide methyl ether, ethylene glycol diacrylate, ethylene glycol dimethacrylate, hexahydro-1,3,5-triacyl-S-triazine, 2,2-bis(acrylamide)acetic acid and the like. Of these, N,N'-methylenebisacrylamide, N,N'-methylenebismethacrylamide, N,N'-(1,2dihydroxyethylene)bisacrylamide, 1,3- diacrylamide methyl-2imidazolidone and diacrylamide methylethylene urea are particularly preferred.

Based on the total amount of these monomers, the monomer of general formula (1) may be used in an amount of from about 70 to 99.8% by weight, preferably from 80 to 99% by weight, the cationic acrylamide monomer in an amount of from about 0.1 to 10% by weight, preferably from 0.5 to 10% by weight, and the water-soluble cross-linking monomer from about 0.1 to 20% by weight, preferably from 0.5 to 10% by weight.

If desired, other water-soluble monomers capable of copolymerizing with the monomer of general formula (1) may be used in an amount of about 0.01 to 10% by weight.

Examples of the biocatalyst to be immobilized by entrapping in the aforementioned immobilization carrier include enzymes, microorganisms, organella, animal and plant cells, and they may be used in the purified or disrupted forms, with no particular limitation in terms of their origin or form. For example, any genus of microorganism including bacteria, actinomycetes, yeasts, fungi and the like can be used, such as those belonging to the genera Brevibacterium, Corynebacterium, Rhodococcus, Gordona, Vibrio, Nitrosomonas, Streptococcus, Lactobacillus, Bacillus, Azotobacter, Nocardia, Saccharomyces, Endomyces, Asmergillus, Penicillium, Mucor, Rhizopus and the like.

The immobilized biocatalyst of the present invention can be prepared, for example, by adding a mixture of the monomers to a suspension of a biocatalyst, further adding a commonly used polymerization initiator and accelerator, such as potassium persulfate and N,N,N',N'-tetramethylethylene-diamine, to the suspension, and then incubating the resulting mixture at a pH value of from about 5 to 10, preferably from 6 to 8, at a temperature of from about 0° to 50° C., preferably from 0° to 35° C., for about 15 to 120 minutes, thereby effecting polymerization and gelation.

The biocatalyst content in the polymerized gel varies depending on the type, form and the like of each biocatalyst to be used, but the content may be in the range of generally from about 0.1 to 40% by weight, preferably from 1 to 20% by weight. The content of monomers in the polymerization reaction solution may be in the range of generally from about 2 to 30% by weight, preferably from 5 to 15% by weight.

These immobilized biocatalysts may be made into any shape such as granules, films, plates and the like.

The use of the biocatalyst immobilization carrier of the present invention renders possible the preparation of immobilized biocatalysts which are excellent in storage stability and simultaneously have the strength and the like advantages of the prior art high polymer base carriers, especially polyacrylamide base carriers. The immobilized biocatalyst of the present invention does not putrefy even after one month of storage at ordinary temperature and therefore is extremely stable.

The following examples are provided to further illustrate the present invention. It is to be understood, however, that the examples are for the purpose of illustration only and are not intended as a definition of the limits of the present invention. The terms "part(s)" and as used herein are based on weight, unless otherwise indicated.

EXAMPLE 1

*Rhodococcus rhodochruos* strain J-1 (FERM BP-1478) was aerobically cultured, and the resulting cells were washed and concentrated to prepare a cell suspension (15% as dry cells) for use in immobilization. 16 parts of 50 mM potassium phosphate buffer (pH 7.0, this is to be repeated in the following) and 10 parts of a monomer mixture solution composed of 92% N,N-diethylacrylamide, 3% N,N-dimethylaminopropylacrylamide and 5% N,N'-methylenebisacrylamide were added to 70 parts of the concentrated cell suspension cooled in an ice bath. The mixture was subsequently stirred in an ice bath to obtain a uniform suspension. 2 parts of 10% N,N,N',N'-tetramethylethylenediamine aqueous solution and 2 parts of 10% ammonium persulfate aqueous solution were added, followed by 1 hour of incubation at a temperature of 35° C. or lower to effect polymerization and gelation. The thus obtained block of immobilized cells was cut into small particles and washed with water to be evaluated as a sample of immobilized cells.

When a 20 g portion of the thus prepared sample was soaked in 80 g of 0.5% sodium sulfate aqueous solution contained in a polyethylene bottle and stored at 30° C. for one month after sealing the bottle, no changes in appearance were found and contamination of microorganisms was extremely low.

COMPARATIVE EXAMPLE 1

As a comparison, a sample of immobilized cells was prepared using an acrylamide base immobilization carrier. 1 part of 50 mM potassium phosphate buffer (pH 7.0) and 25 parts of a 40% monomer mixture aqueous solution composed of 92% acrylamide, 3% N,N-dimethylaminopropyl methacrylate and 5% N,N'-methylenebisacrylamide were added to 70 parts of the concentrated cell suspension. 2 parts of 10% N,N,N',N'-tetramethylethylenediamine aqueous solution and 2 parts of 10% ammonium persulfate aqueous solution were added to this mixture. Thereafter, polymerization and washing were carried out in the same manner as described in Example 1.

When the prepared sample was soaked in 0.5% sodium sulfate aqueous solution and stored at 30° C. for one month in the same manner as described in Example 1, growth of a markedly large number of contaminated microorganisms and generation of a strong rotted odor as well as turbidity were observed.

EXAMPLES 2 TO 6 AND COMPARATIVE
EXAMPLES 2 TO 6

Immobilized biocatalysts were prepared by changing types and concentrations of monomers and biocatalysts and evaluated, in the same manner as in Example 1 and Comparative Example 1. The results are shown in Table 1.

In this instance, the immobilized biocatalysts were stored at 30° C. for one month by soaking them in 100 mM potassium phosphate buffer (pH 7) in the case of Examples 2 to 4 and Comparative Examples 2 to 4 or in 0.9% sodium chloride aqueous solution in the case of Examples 5 and 6 and Comparative Examples 5 and 6.

Putrefaction was judged based on the degree of odor generated from, and turbidity formed in, the soaking solution.

In the table, results of the evaluation are shown by 5 degrees where 0 means no putrefied odor or turbidity of the soaking solution and 4 means maximum odor or turbidity.

TABLE 1

| | Monomers | | | Biocatalysts | | Putrefaction | |
|---|---|---|---|---|---|---|---|
| | | Ratio | Conc. | | Conc. | | |
| Run No. | Name | (%) | (%) | Strain | (%) | Odor | Turbidity |
| Ex. 2 | N,N-Dimethylacrylamide | 92 | | | | | |
| | N,N-Dimethylaminopropyl methacrylamide | 5 | 10 | Rhodococcus sp. EA4 (FERM P-12136) | 10 | 0 | 0 |
| | N,N'-Methylenebis-acrylamide | 3 | | | | | |
| Comp. EX. 2 | Acrylamide | 92 | | | | | |
| | N,N-Dimethylaminopropyl methacrylate | 5 | 10 | Rhodococcus sp. EA4 (FERM P-12136) | 10 | 3 | 4 |
| | N,N'-Methylenebis-acrylamide | 3 | | | | | |
| Ex. 3 | N,N-Diethylacrylamide | 95 | | | | | |
| | N,N-Dimethylaminopropyl methacrylamide quaternary compound | 1 | 10 | Corynebacterium sp. N-771 (FERM BP-959) | 8 | 0 | 0 |
| | N,N'-Methylenebis-acrylamide | 4 | | | | | |
| Comp. Ex. 3 | Acrylamide | 95 | | | | | |
| | N,N-Dimethylaminopropyl methacrylate | 1 | 10 | Corynebacterium sp. N-771 (FERM BP-959) | 8 | 3 | 4 |
| | N,N'-Methylenebis-acrylamide | 4 | | | | | |
| Ex. 4 | N,N-Diethylacrylamide | 92 | | | | | |
| | N,N-Dimethylaminopropyl methacrylamide quaternary compound | 2 | 8 | Gordona terrae MA-1 (FERM BP-4535) | 5 | 0 | 0 |
| | N,N'-Methylenebis-acrylamide | 6 | | | | | |
| Comp. Ex. 4 | Acrylamide | 92 | | | | | |
| | N,N-Dimethylaminopropyl methacrylate | 2 | 8 | Gordona terrae MA-1 (FERM BP-4535) | 5 | 2 | 3 |
| | N,N'-Methylenebis-acrylamide | 6 | | | | | |
| Ex. 5 | N,N-Dimethylacrylamide | 8 | | | | | |
| | N,N-Diethylacrylamide | 5 | | Nocardia sp. N-775 (FERM BP-961) | | | |
| | N,N-Dimethylamino-propylacrylamide | 5 | 10 | | 8 | 0 | 0 |
| | N,N'-Methylenebis-acrylamide | 5 | | | | | |
| Comp. Ex. 5 | Acrylamide | 90 | | | | | |
| | N,N-Dimethylaminopropyl acrylate | 5 | 10 | Nocardia sp. N-775 (FERM BP-961) | 8 | 3 | 3 |
| | N,N'-Methylenebis-acrylamide | 5 | | | | | |
| Ex. 6 | N,N-Diethylacrylamide | 92 | | | | | |
| | N,N-Diethylaminopropyl methacrylamide | 3 | 8 | Brevibacterium sp. R-312 (FERM P-2722) | 4 | 0 | 0 |
| | N,N'-Methylenebis-acrylamide | 5 | | | | | |
| Comp. Ex. 6 | Acrylamide | 92 | | | | | |
| | N,N-Dimethylaminopropyl methacrylate quaternary compound | 3 | 8 | Brevibacterim sp. R-312 (FERM P-2722) | 4 | 2 | 3 |
| | N,N'-Methylenebis-acrylamide | 5 | | | | | |

While the invention has been described in detail and with reference to specific examples thereof, it will be apparent to one skilled in the art that various changes and modifications can be made therein without departing from the spirit and scope of the invention.

What is claimed is:

1. An immobilized biocatalyst consisting essentially of polymer gel entrapping a biocatalyst wherein the polymer gel is a copolymer of an N,N-dialkylacrylamide monomer selected from the group consisting of N,N-dimethylacrylamide and N,N-diethylacrylamide in an amount of from about 70 to about 99.8% by weight with a cationic acrylamide monomer selected from the group consisting of N,N-dimethylaminopropylacrylamide, N,N-dimethylaminopropylmethacrylamide, N,N-diethylaminopropylmethyacrylamide, N,N- diethylaminopropylacrylamide and quaternary compounds thereof in an amount of from about 0.1 to about 10% by weight and a water-soluble cross-linking monomer selected from the group consisting of N,N'-methylenebisacrylamide, N,N'-methylenebismethacrylamide, N,N'-(1,2-dihydroxyethylene) bisacrylamide, 1,3-diacrylamide methyl-2-imidazolidone and diacrylamide methylethylene urea in an amount of from about 0.1 to about 20% by weight.

2. The immobilized biocatalyst of claim 1 wherein the biocatalyst is selected from the group consisting of enzymes, bacteria, actinomycetes, fungi, organelles, animal cells and plant cells.

3. A method for immobilizing a biocatalyst in a polymer gel consisting essentially of the steps of:

(i) forming a mixture containing a biocatalyst and monomers wherein the monomers are an N,N-dialkylacrylamide monomer selected from the group consisting of N,N-dimethylacrylamide and N,N-diethylacrylamide in an amount of from about 70 to about 99.8% by weight, a cationic acrylamide monomer selected from the group consisting of N,N-dimethylaminopropylacrylamide, N,N-dimethylaminopropylmethacrylamide, N,N-diethylaminopropylmethacrylamide, N,N-diethylaminopropylacrylamide and quaternary compounds thereof in an amount of from about 0.1 to about 10% by weight and a water-soluble cross-linking monomer selected from the group consisting of N,N'-methylenebisacrylamide, N,N'-methylenebismethacrylamide, N,N'-(1,2-dihydroxyethylene) bisacrylamide, 1,3-diacrylamide methyl-2-imidazolidone and diacrylamide methylethylene urea in an amount of from about 0.1 to about 20% and (ii) copolymerizing the monomers in the mixture to form a polymer gel entrapping the biocatalyst.

4. The method for immobilizing a biocatalyst of claim 3 wherein the biocatalyst is selected from the group consisting of enzymes, bacteria, actinomycetes, fungi, organelles, animal cells and plant cells.

5. The immobilized biocatalyst of claim 2 wherein the fungi is yeasts.

6. The method of immobilizing a biocatalyst of claim 4 wherein the fungi is yeasts.

* * * * *